(12) United States Patent
Simon

(10) Patent No.: US 8,080,629 B2
(45) Date of Patent: Dec. 20, 2011

(54) POLYMER MATERIAL USEFUL FOR MEDICAL DEVICES

(75) Inventor: Peter F. W. Simon, Reinbek (DE)

(73) Assignee: GKSS-Forschungszentrum Geesthacht GmbH, Geesthacht (DE)

( * ) Notice: Subject to any disclaimer, the term of this patent is extended or adjusted under 35 U.S.C. 154(b) by 572 days.

(21) Appl. No.: 12/223,811

(22) PCT Filed: Feb. 12, 2007

(86) PCT No.: PCT/EP2007/001194
§ 371 (c)(1),
(2), (4) Date: Dec. 16, 2008

(87) PCT Pub. No.: WO2007/090686
PCT Pub. Date: Aug. 16, 2007

(65) Prior Publication Data
US 2009/0234375 A1    Sep. 17, 2009

(30) Foreign Application Priority Data
Feb. 10, 2006  (EP) .................................. 06002738

(51) Int. Cl.
*C08G 64/00* (2006.01)
*C08G 63/02* (2006.01)
(52) U.S. Cl. ....................................... 528/271; 528/272

(58) Field of Classification Search ................. 528/271, 528/272
See application file for complete search history.

(56) References Cited

U.S. PATENT DOCUMENTS
6,486,295 B1    11/2002   Gross et al.

FOREIGN PATENT DOCUMENTS
EP    1362872 A1    11/2003
WO    2004/090042 A1    10/2004

OTHER PUBLICATIONS

Schmidt, Annette M., "Bioabbaubare Polymernetzwerk-Systeme mit Formgedächtniseffekt und kristallisierbaren Schaltsegment," Mensch & Buch Verlag, Berlin, XP002260848 (Jun. 6, 2002) (w/English Language Abstract)—[pp. 138-146, figure 5.2].

*Primary Examiner* — Terressa M Boykin
(74) *Attorney, Agent, or Firm* — Sughrue Mion, PLLC

(57) ABSTRACT

A copolymer is described comprising a first repeating unit from a compound selected from the consisting of a pentadecalactone and a dioxanone in combination with a second repeating unit derived from at least one additional ester repeating unit-yielding monomer, wherein the copolymer does not comprise any further repeating units except for said first and second repeating units, a melting temperature of at least 70° C., and a crystalline content selected from the group consisting of an overall crystalline content of at least 25% and a crystalline content of the first repeating unit of at least 20%.

17 Claims, No Drawings

POLYMER MATERIAL USEFUL FOR MEDICAL DEVICES

CROSS REFERENCE TO RELATED APPLICATIONS

This application claims priority under 35 U.S.C. §371 to International Application No. PCT/EP2007/001194 (filed Feb. 12, 2007) which claims priority to European Application No. 06002738.0 (filed Feb. 10, 2006), each of which application are expressly incorporated herein by reference in their entirety.

The present invention concerns polymer materials useful for medical devices as well as medical devices prepared therefrom, including in particular surgical sutures, artificial ligaments, nets for tissue regeneration or vascular plugs. The present invention also concerns a method for preparing such articles, in particular filaments suitable for the preparation of sutures and nets.

Bioabsorbable fibers useful for the manufacture of medical devices are known in the art. U.S. Pat. No. 5,425,984 and EP 024125282 disclose fibers made from a polymer containing from about 15 to about 30 mol % glycolide and absorbable ligament and tendon prostheses made from a polymer of lactide containing up to 10% glycolide as comonomer. One drawback of this conventional material is the fact that the high susceptibility towards hydrolysis of the glycolide polymers renders articles made therefrom unsuitable for applications requiring a long-term stability of the material properties, such as strength, resistance against cycles of changing mechanical loads/forces etc.

One approach addressing the drawbacks associated with the glycolide polymers is the introduction of further comonomers, in particular monomers derived from caprolactone. U.S. Pat. Nos. 4,605,730 and 4,700,704 disclose copolymers of caprolactone and glycolide useful for preparing surgical articles, in particular surgical sutures. These sutures have a Young's modulus of less than 250000 psi. However, the introduction of caprolactone comonomers into glycolide polymers leads also to a reduction in strength. Similar results were also observed with polymer materials comprising lactide monomers as well as trimethylene carbonate monomers, optionally in combination with caprolactone monomers.

U.S. Pat. No. 6,486,295 B1 describes a method to regulate copolymer structure using lipase catalyzed transesterification reactions. This document discloses copolymers comprising caprolactone units and pentadecalactone units. The molecular weight of the polymer disclosed is on average (all values Mn, g/mol) from 10000 to 29000. This document, however, does not disclose any particular suitability of the polyester produced but focuses on the use of lipases for preparing polymer structures. EP1362872 A1 discloses polyester urethanes comprising polypentadecalactone segments wherein the polypentadecalactone segments preferably have a molecular weight (Mn) of from 2000 to 3000.

However, also these materials are not able to maintain a sufficient portion of their initial strength over a prolonged duration of time, a requirement which often is important for medicinal articles, in particular, surgical articles such as those exemplified above.

Accordingly, it is an object of the present invention to provide polymers which enable the preparation of medical articles, in particular, surgical articles such as sutures, nets for tissue regeneration, ligament and tendon prostheses and surgical meshes for hernia repair. The materials aimed for by the present invention shall fulfill at least one of the following requirements:

(1) high strength
(2) optimum hydrolytic stability, i.e. maintaining sufficient strength over a prolonged duration of time even after having been used in a surgical procedure
(3) particle-free degradation properties
(4) minimal elongation under load
(5) resistance towards cycles of changing mechanical forces/loads
(6) stability even under high strain

BRIEF DESCRIPTION OF THE PRESENT INVENTION

The present invention achieves these objects with the polymer as defined in claim 1. Preferred embodiments are outlined in the dependent sub-claims. Furthermore, the present invention provides the surgical articles as defined in the claims and also a method for preparing fibers suitable for the preparation of surgical articles.

DETAILED DESCRIPTION OF THE PRESENT INVENTION

The polymer in accordance with the present invention is a semi-crystalline copolymer comprising repeating units derived from pentadecalactone and/or para-dioxanone (designated also first repeating units) in combination with repeating units derived from at least one further monomer yielding ester repeating units (designated also second repeating units). Preferably the at least one further monomer is selected among caprolactone and para-dioxanone or a mixture thereof. However, in principle any type of ester repeating unit generating monomer may be used as the at least one further monomer. In particular when the copolymer comprises repeating units from dioxanone as the first repeating units the copolymer does not comprise repeating units derived from glycolic acid or derivatives therefrom. A particular preferred embodiment of this kind is a copolymer of para-dioxanone with caprolactone, wherein the repeating units are distributed in the copolymer in block form (dioxanone blocks and caprolactone blocks), preferably linked together by means of a urethane linkage, for example obtained by the below discussed isocyanate linking method. For this embodiment the following description applies, in particular regarding the preferred embodiments concerning molecular weight of the final copolymer as well as of the building blocks, and also concerning the method of synthesis and the mechanical properties.

In another embodiment of the present invention the copolymer is as defined as the other alternative in the main claim, i.e. the copolymer comprises repeating units derived from pentadecalactone in combination with repeating units derived from at least one further monomer yielding ester repeating units.

The copolymer in accordance with one aspect of the present invention has a crystallinity of at least 25% (determined using DSC equipment) and a melting temperature of at least 70° C. Preferably the crystallinity amounts to more than 25%, more preferably more than 30% and in embodiments more than 40% or ever more than 50%. Preferably the upper limit for the crystallinity is 90%, and in embodiments also 80%, 75%, 70% or 60%.

Preferred are copolymers having a number average of the molecular weight of at least 30000, more preferably at least 45000, even more preferably at least 50000 (all values refer to g/mol, determined by GPC analysis versus a polystyrol standard). Copolymers having a number average molecular weight of as high as 75000, and in embodiments more than 100000, preferably more than 150000 (all values refer to g/mol, determined by GPC analysis versus a polystyrol standard) are also envisaged by the present invention.

Preferred are copolymers wherein the different comonomers are distributed within the copolymer in the form of distinct blocks, although also random copolymers are suitable.

Preferred are, however, semi-crystalline phase segregated copolymers, comprising blocks derived from pentadecalactone or dioxanone and blocks derived from the at least one further monomer, preferably selected from caprolactone, para-dioxanone and mixtures thereof. Preferably, the copolymer in accordance with the present invention does not comprise any further repeating units derived from other monomers, except for pentadecalactone, caprolactone and/or para-dioxanone.

The preferred copolymer in accordance with the present invention is a copolymer showing a block-like distribution of the different repeating units within the copolymer. The different blocks of the repeating units may be introduced into the copolymer by means of preformed macromonomers, prepared by conventional polyester chemistry from the above-outlined monomers. These macromonomers preferably are present in the form of diols, i.e. possessing two terminal hydroxyl functionalities. The different blocks, i.e. the macromonomers may then be combined to form the copolymer in accordance with the present invention using diisocyanates in order to prepare urethane linkaging groups for binding the macrodiols to each other. The resulting copolymers can be designated as polyester urethanes, i.e. polymeric structures, comprising blocks corresponding to the initial macromonomers which are polyester segments, bound to each other by means of urethane segments. Preferred diisocyanates for the preparation of the polyester urethanes in accordance with the present invention are compounds of the formula

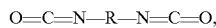

O=C=N—R—N=C=O, wherein R represents a divalent aromatic or aliphatic group. Preferably R is aliphatic, having a carbon chain of from 1 to 10, preferably 2 to 8, more preferably 4 to 7 carbon atoms, preferably a straight chain. This carbon chain can either be saturated with hydrogen (aliphatic unsaturated group) or this chain may show further substituents, preferably short chain alkyl groups having from 1 to 6, more preferably from 1 to 4 carbon atoms, in particular methyl groups. A particular preferred diisocyanate is trimethylhexane-1,6-diisocyanate, another example being hexamethylene diisocyanate.

The macromonomers employed for the preparation of polyester urethanes in accordance with the present invention preferably have a number average molecular weight of from 1000 to 50000 g/mol (as determined by GPC compared to a polystyrene standard), more preferably 1000 to 20000 g/mole and in embodiments more preferably 1500 to 15000 and, in particular, preferably 2000 to 10000. In particular, suitable macromonomers are macrodiols of pentadecalactone having a number average of the molecular weight of from 1000 to 10000, preferably 1500 to 5000, more preferably 2000 to 3000, macrodiols of caprolactone having a number average of the molecular weight of 3000 to 11000, preferably 4000 to 10000 and para-dioxanone macrodiols having a number average of the molecular weight corresponding to the number averages disclosed above for the two other segments. In one embodiment the polymer comprises para-dioxanone macrodiols with an average molecule weight of 2000 to 6000 g/mol, preferably 3000 to 5500 g/mol, in combination with caprolactone derived macrodiols having an average molecular weight of 1500 to 2500, preferably about 2000 g/mol.

As outlined above, the copolymer in accordance with the present invention, i.e. also the polyester urethane in accordance with the present invention preferably has a molecular weight (number average) of at least 50000, in particular 50000 to 200000, more preferably 60000 to 190000 (g/mol, determined by GPC in comparison to a polystyrene standard). Particularly preferred are high molecular weight triblock copolymers, comprising for example one block derived from pentadecalactone and two blocks derived from other ester repeating units or vice versa. Such triblock copolymers can be prepared using suitable macromonomers in suitable ratios, using in particular the above outlined isocyanate linking technology.

The copolymers in accordance with the present invention comprise preferably blocks derived from pentadecalactone wherein the macrodiol corresponding to the pentadecalactone block in the final copolymer has a melting point of at least 20° C., preferably more than 25° C. and in embodiments more than 30° C. or even 35° C.

The copolymers in accordance with the present invention preferably comprise pentadecalactone in an amount of from 10 to 90% by weight, more preferably 25 to 60% and more preferably 30 to 50%. Particularly preferred copolymers in accordance with the present invention are copolymers showing a ratio of pentadecalactone to the further comonomers of from 40/60 to 30/70.

With respect to the above-described preferred embodiment wherein the polymer comprises para-dioxanone macrodiols in combination with caprolactone derived macrodiols, it is further preferred when para-dioxanone derived segments and a caprolactone derived segments are present in the final polymer in a weight ratio of about 1:1, so that approximately equal weights of dioxanone units and caprolactone units are present. In this connection, it is furthermore preferred when the macrodiols are linked by means of the above-described reaction using diisocyanates and, in this connection; it is particularly preferred when diisocyanate employed is hexamethylene diisocyanate. These polymers preferably show an average molecular weight (Mn) of from 45000 to 60000, preferably about 50000 g/mol. Such a polymer preferably shows a melting temperature, being defined at the peak maximum of a DSC measurement (defined as the maximum of the heat flow dQ/dT, see also the below cited reference R. F. Schwarzl) carried out under nitrogen and between −70° C. and 150° C. with a heating and cooling rate of 10 K/min, wherein a peak is recorded in the second cycle, of preferably above 90° C., such as from 90 to 98° C., for example 95 or 96° C.

Preferably such a polymer displays a crystalline content with respect to the segments derived from para-dioxanone of above 20%, such as from 20 to 60%, preferably 25 to 50%, again determined by DSC (second cycle, heating and cooling conditions and temperature range as indicated above, also designated calorie metric crystallinity, obtained by comparing the measured enthalpy increase with the value extrapolated for a 100% crystalline substance, see also F. R., Schwarzl, Polymer-Mechanik, Springer Verlag Berlin Heidelberg 1990, p. 278).

As outlined above, in other embodiments the copolymers in accordance with the present invention possess a melting point of at least 70° C. and preferably a crystallinity of at least 25%.

The above-discussed copolymers in accordance with the present invention and in particular the preferred embodiments as derivable from the above are suitable for the preparation of medical articles, in particular surgical articles, including preferably sutures, surgical nets and meshes, in particular surgical measures for hernia repair, as well as prosthetic tendons and ligaments and vascular plugs. Fibers and filaments prepared from the copolymers in accordance with the present invention enable the preparation of improved surgical articles, such as those exemplified above. Due to the structure of the copolymer in accordance with the present invention it is possible to prepare medicinal articles showing a good balance of mechanical properties in association with a desired degradation profile. As identified above the copolymers in accordance with the present invention enable in particular the preparation of fibres having high strength and sufficient hydrolytic stability so that the mechanical properties can be maintained for a desired time period.

Surgical articles prepared from the copolymers in accordance with the present invention are fully resorbed by the body after surgery in less than 3 years, while retaining at least 50% of the original strength for at least 3 weeks after surgery, preferably at least 6 weeks after surgery.

Monofilaments prepared from the copolymers in accordance with the present invention show an elastic modulus of more than 1000 MPa, preferably more than 1200 MPa and in embodiments more than 1500 MPa. Further they display a tensile strength of more than 100 MPa, at an elongation of less than 1200%, preferably of more than 120 MPa and in embodiments more than 150 MPa. Typical monofilaments in accordance with the present invention can be prepared from the copolymers in accordance with the present invention having diameters of between 750 and 25 µm, preferably 600 to 30 µm, more preferably 500 to 40 µm. The copolymers in accordance with the present invention can also be processed to multifilaments wherein again the single filaments within the multifilament material show a filament diameter in accordance with the ranges outlined above for the monofilament. Monofilaments and multifilaments in accordance with the present invention enable the preparation of surgical articles, such as sutures, surgical measures and nets, in particular for tissue regeneration and hernia repair, as well as prosthetic tendons and ligaments satisfying the highest requirements with respect to maintenance of strength after surgery. At the same time, these surgical articles are biocompatible and may be resorbed by the body, so that the use of these materials in the medicinal field is plausible.

The present invention furthermore provides a method for preparing filaments from the copolymers in accordance with the present invention. This method preferably comprises the melt spinning of a copolymer in accordance with the present invention using standard melt spinning equipment. Preferably, melt spinning is conducted using a pre-dried polymer granulate (for example, pre-dried at a pressure of 0.1 mbar at 40° C. for more than 24 hours). This pre-dried product can then be stored, preferably under moisture reducing or moisture excluding conditions, for example, at slightly increased temperature using a gas phase in contact with the copolymer having a very low thaw point, such as a thaw point of below −10° C., preferably below −15° C. This pre-dried material can then be introduced into an extruder, preferably a single screw extruder having distinct zones for adjusting a temperature profile. A suitable extruder has, in particular, at least three different temperature zones, which can be regulated for the processing of the copolymers in accordance with the present invention to temperature in the ranges of 130 to 170° C., 150 to 200° C. and 150 to 210° C., respectively. It is possible to have one or more zones of lower temperature at the inlet, such as having 20 to 100° C. and to increase the temperature at the outlet of the extruder to slightly higher values, such as from 115 to 215° C. After leaving the extruder, the molten extrudate is fed using a suitably heated (150 to 215° C.) line to an optional filter unit (having a pore size of from 50 to 250 µm, preferably 50 to 10 µm, followed by feeding the melt to a spinning nozzle being provided in a suitable heated (160 to 220° C.) spinner head. The nozzle has at least one opening of a usual size and design enabling the preparation of desired monofilament or multifilaments. After leaving the spinning nozzle, the produced filaments are preferably cooled by means of blowing air having a temperature of between 0 and 50° C., preferably 4 to 40° C. The span filaments can then be wound onto suitable devices. As alternative, it is possible to cool the fibers using a water bath having a temperature similar to the temperature discussed above in connection with the blowing air. Such a water bath usually has a length of from 10 to 200 cm. The span filaments can then be again wound onto suitable devices. During cooling, after cooling prior to storage or after storage, the filaments in accordance with the present invention may be subjected to further standard processing steps, such as stretching etc., in order to further modify the filament properties.

The filaments prepared in accordance with the above process, or prepared by any other standard procedure, may be advantageously used for the preparation of the surgical articles discussed above. It is in this connection also possible to use other molding processes, such as extrusion processes, injection-molding processes etc., depending on the type of the surgical article desired.

The filaments of the invention preferably comply with the requirements for "Sterile, resorbierbare, synthetische Fäden; Fila resorbilia synthetica monofilamenta sterilia", Europäisches Arzneibuch, 3. Ausgabe, 1997, S. 1321 f.f., so that e.g. their length and diameter is constant as specified therein, they withstand the given forces until break with and without needle, and are packed and labelled accordingly.

The filaments of the invention have a high reproducibility concerning the force that is excerted when triggering the change from temporary to permanent shape. As knots can be tied from shape memory filaments by triggering the shape memory effect, the force that is exerted when using the material of the invention is much more reproducible than when tieing by hand and even when using known shape memory polymers. Therefor such shape memory filaments have lower requirements concerning the tearing resistance than known suture materials, what allows to optimize other properties.

In another preferred embodiment the filaments of the invention therefore only withstand a lower force until break than the force specified in the Europäisches Arzneibuch cited above, but are advantageous over known filaments in other parameters (e.g. elasticity, biodegradability, biocompatibility, etc.)

The copolymers which are processed to yield the articles as outlined above may either be the pure copolymers or they may be compounded previously or during processing with conventional additives, such as active principles, contrast agents, diagnostic agents, filler, etc. These additives may be used in conventional amounts as long as they do not interfere with the desired end property of the surgical article.

EXAMPLE

Suture Formed of Biodegradable Shape Memory Polymer

1. Synthesis of Biodegradable Shape Memory Polymer

In the first step of the synthesis, macrodiols were synthesized via ring opening polymerization with a low molecular weight diol as initiator and purified according to reported methods (A. Lendlein, P. Neuenschwander, U. W. Suter, *Macromol. Chem. Phys.*, 201, 1067, (2000)). Oligo(ε-caprolactone)diol ($M_n$ 2000 g/mol) was chosen as precursor for the switching segments (soft segments) having a melting transition temperature ($T_{trans}$). Crystallizable oligo(p-dioxanone)

diol ($M_n$ 4000 g/mol) with a melting transition temperature ($T_m=T_{perm}$) was chosen as hard segment to provide the physical crosslinks.

In the second step, the two macrodiols were coupled with hexamethylene diisocyanate as follows: equal weights of both macrodiols were dissolved in 1,2-dichloroethane and heated to 80° C. An equimolar amount of hexamethylene diisocyanate was added. The synthesis was carried out under exclusion of water; solvents and monomers were dried by standard techniques. The crude product was precipitated in hexane. The resulting polymer has a molecular weight ($M_n$) of about 50 000 g/mol, the melting temperature Tm was greater than 90° C. and the crystallinity due to the oligo(p-dioxanone)diol segments was about 35%.

2. Shape Memory Property of the Biodegradable Memory Polymer

To quantify shape memory properties, programming and recovery were investigated by cyclic thermomechanical tests as follows: the material was pressed to films having a thickness of 300-500 µm. Dog-bone shaped samples (length between clamps: 6 mm, width: 3 mm) were punched out of the films and mounted in a tensile tester equipped with a thermo-chamber (see K. Sakurai, Y. Shirakawa, T. Kahiwagi, T. Takahashi, *Polymer* 35, 4238 (1994)). The tests were carried out at 200% strain at a strain rate of 10 mm·min$^{-1}$ with $T_{low}=-20°$ C. and $T_{high}=50°$ C. The samples were held at $T_{low}$ for 10 min before removing load (see H. Tobushi, H. Hara, E. Yamada, S. Hayashi, *S.P.I.E.* 2716, 46 (1996)).

This simple test describes shape memory in one dimension, however, the effect takes place in all three dimensions. The effect is commonly described using two important parameters. The strain fixity rate $R_f$ describes the ability of the switching segment to fix the mechanical deformation which has been applied during the programming process. For the polymer described herein, $R_f$ is about 99%. The strain recovery rate $R_r$ quantifies the ability of the material to recover its permanent shape. $R_r$ depends on the cycle number and gradually approaches 100% because of reorientation of the polymer chains in the unoriented, pressed films during the early cycles, due to inelastic behavior. In the first cycle, $R_f$ is about 80% for the disclosed multiblockcopolymer and is about 100% in the third cycle.

3. In vitro Test of Biocompatibility

The tissue-compatibility of the polymers described herein was investigated using chorioallantoic membrane tests (CAM-tests) which are a sensitive method to evaluate toxicity (K. Spanel-Borowski, *Res. Exp. Med. (Berl)* 189, 69 (1989)). Nine separate experiments were carried out. All tests showed good tissue-compatibility when graded according to Folkman (R. Crum, S. Szabo, J. Folkman, *Science* 230, 1375 (1985)). The test results showed that there was no detectable change in the number or shape of blood vessels or damage under or in the vicinity of the polymer film (sample length: left $\overline{A}$0.3 cm, right $\overline{A}$0.5 cm). For a positive control sample, see A. Lendlein, *Chem. in unserer Zeit* 33, 279 (1999).

4. In vitro Test of the Tying of a Suture Knot

The highly elastic shape memory thermoplastics was extruded into monofilaments by extrusion at 90° C. through a rod die on a Haake Polylab single-screw extruder. Sutures sterilized with ethylene oxide at 45° C. were programmed under sterile conditions by exerting a controlled stress on the extruded fiber and subsequent thermal quenching. Sutures that are 0.29 mm in diameter were thereby obtained. A loose knot was tied and the filament held fixed on both sides. On warming of the filament above 40° C., the knot contracted exerting a maximum force, that was highly reproducible when repeating the experiment for 10 times and was almost independent from the temperature, as long as it was high enough to trigger the change in shape and not near $T_m$. This reproducibility allows to use filaments for suture, that have a lower resistance in break tests than known materials.

What is claimed is:

1. A copolymer, comprising:
   a first repeating unit derived from a compound selected from the group consisting of a pentadecalactone and a dioxanone in combination with a second repeating unit derived from at least one additional ester repeating unit yielding monomer, wherein the copolymer does not comprise any further repeating units except for said first and said second repeating units,
   a melting temperature of at least 70° C., and
   a crystalline content selected from the group consisting of an overall crystalline content of at least 25% and a crystalline content of the first repeating unit of at least 20%.

2. The copolymer of claim 1, wherein the first repeating unit and the second repeating unit are distributed within the copolymer in distinct blocks.

3. The copolymer of claim 1, wherein the copolymer has a number average of the molecular weight of at least 50000 g/mol.

4. The copolymer of claim 1, wherein the copolymer has a melting temperature of at least 80° C.

5. The copolymer of claim 1, wherein the copolymer has a crystallinity of at least 35%.

6. The copolymer of claim 1, wherein the copolymer is a polyester urethane, comprising blocks of the first repeating unit and blocks of the second repeating unit connected with a divalent urethane segment.

7. The copolymer of claim 6, wherein a block derived from pentadecalactone has a number average of the molecular weight of 1000 to 20000 g/mol.

8. The copolymer of claim 1, wherein the first repeating unit of pentadecalactone comprises 10 wt % to 90 wt %.

9. The copolymer of claim 1, wherein the at least one additional ester repeating units yielding monomer is selected from the group consisting of caprolactone, para-dioxanone and mixtures thereof.

10. A surgical article, comprising a copolymer of claim 1.

11. The surgical article of claim 10, wherein the surgical article is selected from the group consisting of sutures, surgical nets and measures.

12. A filament, prepared from a copolymer of claim 1, wherein the filament has an average diameter from 500 µm to 40 µm.

13. The filament of claim 12, wherein the filament has at least one quality selected from the group consisting of an elastic modulus of more than 1000 Mpa and a tensile strength of more than 100 MPa at an elongation of less than 1200%.

14. The surgical article of claim 11, wherein the sutures, surgical nets and measures are adapted for a use selected from the group consisting of hernia repair, prosthetic tendons and prosthetic ligaments.

15. A method of making a filament comprising the steps of:
   a) selecting a copolymer of claim 1,
   b) melting the copolymer,
   c) extruding the molten copolymer through a spinning nozzle to form a filament,
   d) cooling of the filament, and
   e) winding the filament onto a suitable device.

16. The method of claim 15, further comprising a step of admixing the copolymer with a conventional additive, between step a) and step b).

17. The method of claim 15, further comprising a step of admixing the copolymer with a conventional additive, between step b) and step c).

* * * * *